US00PP25065P3

(12) United States Plant Patent
Radler

(10) Patent No.: US PP25,065 P3
(45) Date of Patent: Nov. 18, 2014

(54) SHRUB ROSE PLANT NAMED 'RADCLEOME'

(50) Latin Name: *Rosa hybrida*
Varietal Denomination: Radcleome

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 106 days.

(21) Appl. No.: 13/507,959

(22) Filed: Aug. 9, 2012

(65) Prior Publication Data

US 2014/0047587 P1 Feb. 13, 2014

(51) Int. Cl.
*A01H 5/00* (2006.01)

(52) U.S. Cl.
USPC ..... Plt./107

(58) Field of Classification Search
CPC ..... A01H 5/0222; A01H 5/0216; A01H 5/02; A01H 5/00
USPC ..... Plt./107
See application file for complete search history.

*Primary Examiner* — Kent L Bell
(74) *Attorney, Agent, or Firm* — Buchanan, Ingersoll & Rooney, PC

(57) ABSTRACT

A new and distinct shrub rose plant is provided that abundantly forms in clusters attractive small single medium pink finishing to light pink blossoms that drop their petals well upon full maturity. The plant exhibits vigorous vegetation and an upright and bushy growth habit. The foliage is dark green with a semi-glossy finish on the upper surface. The disease resistance is excellent, particularly with respect to Black Spot, Powdery Mildew, and Rust. The plant is well suited for growing as attractive ornamentation in in the landscape as a hedge or mass planting. Alternatively, the plant can be grown in containers.

1 Drawing Sheet

Botanical/commercial classification: *Rosa hybrida*/Shrub Rose Plant.

Varietal denomination: cv. Radcleome.

SUMMARY OF THE INVENTION

The new variety of *Rosa hybrida* landscape shrub rose plant of the present invention was created during 2001 at Greenfield, Wis., U.S.A., by open pollination in a rose garden setting at my home in the hope that desired characteristics would be displayed in the progeny. The female parent (i.e., the seed parent) was the 'Angel Rose' variety (non-patented in the United States). The female parent is a Polyantha rose and sometimes is identified as 'Minima'. The male parent (i.e., the pollen parent) is unknown. The parentage of the new variety can be summarized as follows:

'Angel Rose'×Unknown.

The seeds resulting from the above pollination were sown and small plants were obtained which were physically and biologically different from each other. Selective study resulted in the identification of a single plant of the new variety.

It was found that the new Landscape Shrub rose plant of the present invention possesses the following combination of characteristics:

(a) abundantly forms in clusters attractive small single medium pink finishing to light pink blossoms that drop their petals well upon fully maturity,
(b) exhibits an upright and bushy growth habit,
(c) forms vigorous vegetation,
(d) forms attractive dark green foliage with a semi-glossy finish on the upper surface that contrasts well with the blossom coloration, (e) exhibits excellent disease resistance, and
(f) is well suited for growing as attractive ornamentation in the landscape.

A new rose variety is provided which bears attractive single light blossoms combined with excellent disease resistance, particularly with respect to Black Spot, Powdery Mildew, and Rust. Commonly more than 50 blooms per stem are formed which attract bees. The plant has been found to develop well regardless of the mode used for asexual propagation.

The new variety well meets the needs of the horticultural industry. It can be grown to advantage as ornamentation in parks, gardens, public areas, and in residential settings. The new variety is particularly well suited for growing as a hedge or as a mass planting. The new variety also can be grown in containers.

The new variety of the present invention also can be readily distinguished from its 'Angel Rose' parent as well as from other Polyantha hybrid varieties, such as the 'Harpballred' variety (U.S. Plant Pat. No. 24,437). More specifically, the 'Angel Rose' female parent forms semi-double to double blossoms having hues of pink to white. The 'Harpballred' variety has a generally smaller stature and forms dissimilar bright red blossoms with a white eye.

The characteristics of the new variety have been found at Wasco, Calif., U.S.A., and near West Grove, Pa., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radcleome', and is being marketed under the LOOK-A-LIKES and PHLOXY BABY trademarks.

BRIEF DESCRIPTION OF THE PHOTOGRAPH

The accompanying photograph shows, as nearly true as it is reasonably possible to make the same in a color illustration of this character, typical flowering rose plants of the new variety. The illustrated rose plants of the new variety were approximately three years of age and were observed during June while growing outdoors on their own roots near West Grove, Pa., U.S.A.

DETAILED BOTANICAL DESCRIPTION

The chart used in the identification of colors is that of The Royal Horticultural Society (R.H.S. Colour Chart—1995 Edition or equivalent), London, England. The description is based on the observation of three-year-old specimens of the new variety during June while growing outdoors on their own roots near West Grove, Pa., U.S.A.

Class: Landscape Shrub Rose, Polyantha Hybrid.

Plant:

*Height*.—Approximately 5.5 feet on average at full maturity.

*Width*.—Approximately 4 to 5 feet on average at full maturity.

*Habit*.—Upright and bushy.

Branches:

*Length*.—Commonly approximately 64 cm on average.

*Diameter*.—Commonly approximately 0.5 cm on average.

*Color*.—Near Yellow-Green Group 144B on young stems, and Brown Group 200D with areas of Greyed-Orange Group 165B on adult wood.

*Texture*.—Generally smooth on young stems and somewhat rough on adult wood.

*Thorns*.—Size: commonly approximately 5 mm in length on average. Quantity: numerous. Color: commonly near Yellow-Green Group 144C on young stems, and near Greyed-Orange Group 166B overlaid with Greyed-Orange Group 166A at the apex.

Leaves:

*Size*.—Commonly approximately 9 cm in length on average and approximately 6 cm in width on average for a five-leaflet leaf.

*Leaflets*.—Number: 3, 5, and 7. Length: approximately 4 cm on average for a terminal leaflet, and approximately 2.3 cm on average for a lower leaflet. Width: approximately 2 cm on average for a terminal leaflet, and approximately 1.4 cm on average for a lower leaflet. Shape: ovate with a rounded base and an acuminate tip. Margins: serrate. Texture: generally smooth on the upper surface and more rugose on the under surface. Overall appearance: attractive dark green leaves with a glossy upper surface. Color: (when young): Upper surface: near Green Group 143A. Under surface: near Yellow-Green Group 144A. Color (when fully mature): Upper surface: commonly a blend of Yellow-Green Group 146A and Yellow-Green Group 147A. Under surface: Green Group 138A.

*Petioles*.—Length: commonly approximately 2.5 cm on average. Diameter: commonly approximately 1 mm on average. Color: near Green Group 143A.

*Rachis*.—Length: approximately 7 cm on average. Diameter: approximately 1 mm on average. Color: near Green Group 139B.

*Stipules*.—Number: two per leaf. Length: commonly approximately 1.5 cm on average. Width: commonly approximately 1 mm on average. Shape: generally lanceolate. Color: upper surface: near Green Group 143A. Color: lower surface: near Yellow-Green Group 144A.

Inflorescence:

*Flowering season*.—Commonly during May and June for approximately two months at West Grove, Pa., U.S.A.

*Number of flowers*.—Commonly approximately 6 or 15 blooms on average in a cluster, and approximately 200 blooms on a plant at a given time.

*Peduncle*.—Near Yellow-Green Group 144A in coloration, commonly approximately 1 cm in length, and smooth in texture.

*Sepals*.—Upper surface: covered with short hairs, and commonly near Yellow-Green Group 145A in coloration. Under surface: covered with short hairs, and Yellow-Green Group 144A in coloration. Shape: generally lanceolate. Size: commonly approximately 9 mm in length on average, and approximately 3 mm in width at the base. Number: five. Apex: cuspidate. Margin: entire, commonly two or three sepals have extensions up to approximately 3 mm in length.

*Buds*.—Shape: generally ovoid. Length: approximately 5 mm on average as the calyx breaks. Diameter: approximately 4 mm on average as the calyx breaks. Color: near Red-Purple Group 63A when opening.

*Flower*.—Form: cup-like, single. Diameter: approximately 2 cm on average when fully open. Depth: commonly approximately 5 mm. Color (when opening): Upper surface: near Red-Purple Group 63B with White Group 155B at the base. Under surface: near Red-Purple Group 63C with Yellow-White Group 158D at the base. Color (at end of blooming): Upper surface: near Red-Purple Group 62B with White Group 155A at the base. Under surface: near Red-Purple Group 69A with White Group 155A at the base. Fragrance: none noticeable. Petal number: commonly approximately 5 on average under normal growing conditions. Petal length: commonly approximately 1.2 cm on average. Petal width: commonly approximately 8 mm on average. Petal shape: narrowly obcordate. Petal margin: entire. Petal apex: obcordate. Petal base: cuneate. Lastingness: commonly approximately 3 to 5 days depending upon environmental conditions. Petal drop: good, the petals commonly detach cleanly and freely drop upon full maturity. Stamen number: approximately 38 on average. Anthers: Yellow-Orange Group 17A in coloration. Filaments: approximately 5 mm in length, and Yellow-Group 5B in coloration. Pollen: Yellow-Orange Group 17A in coloration. Pistils: separate and free, and commonly number approximately 10 on average. Styles: commonly approximately 1 mm in length and near Yellow-Green Group 145D in coloration. Stigma: commonly less than 1 mm in width and Green Group 139D in coloration. Receptacle: commonly spherical in shape, approximately 2 mm in diameter, smooth in texture, near Yellow-Green Group 144A in coloration, with achenes commonly being present on the bottom and wall.

Development:

*Vegetation*.—Vigorous and strong.

*Blossoming*.—Abundant.

*Resistance to diseases*.—Excellent, particularly with respect to Blackspot, Powdery Mildew, and Rust.

*Hardness*.—U.S.D.A. Hardiness Zone Nos. 5 to 9.

Plants of the 'Radcleome' variety have not been observed under all possible environmental conditions to date. Accordingly, it is possible that the phenotypic expression may vary somewhat with changes in light intensity and duration, cultural practices, and other environmental conditions.

I claim:

1. A new and distinct Shrub rose plant characterized by the following combination of characteristics:

(a) abundantly forms in clusters attractive small single medium pink finishing to light pink blossoms that drop their petals well upon full maturity, (b) exhibits an upright and bushy growth habit, (c) forms vigorous vegetation, (d) forms attractive dark green foliage with a semi-glossy finish on the upper surface that contrasts well with the blossom coloration, (e) exhibits excellent disease resistance, and (f) is well suited for growing as attractive ornamentation in the landscape;

substantially as herein shown and described.

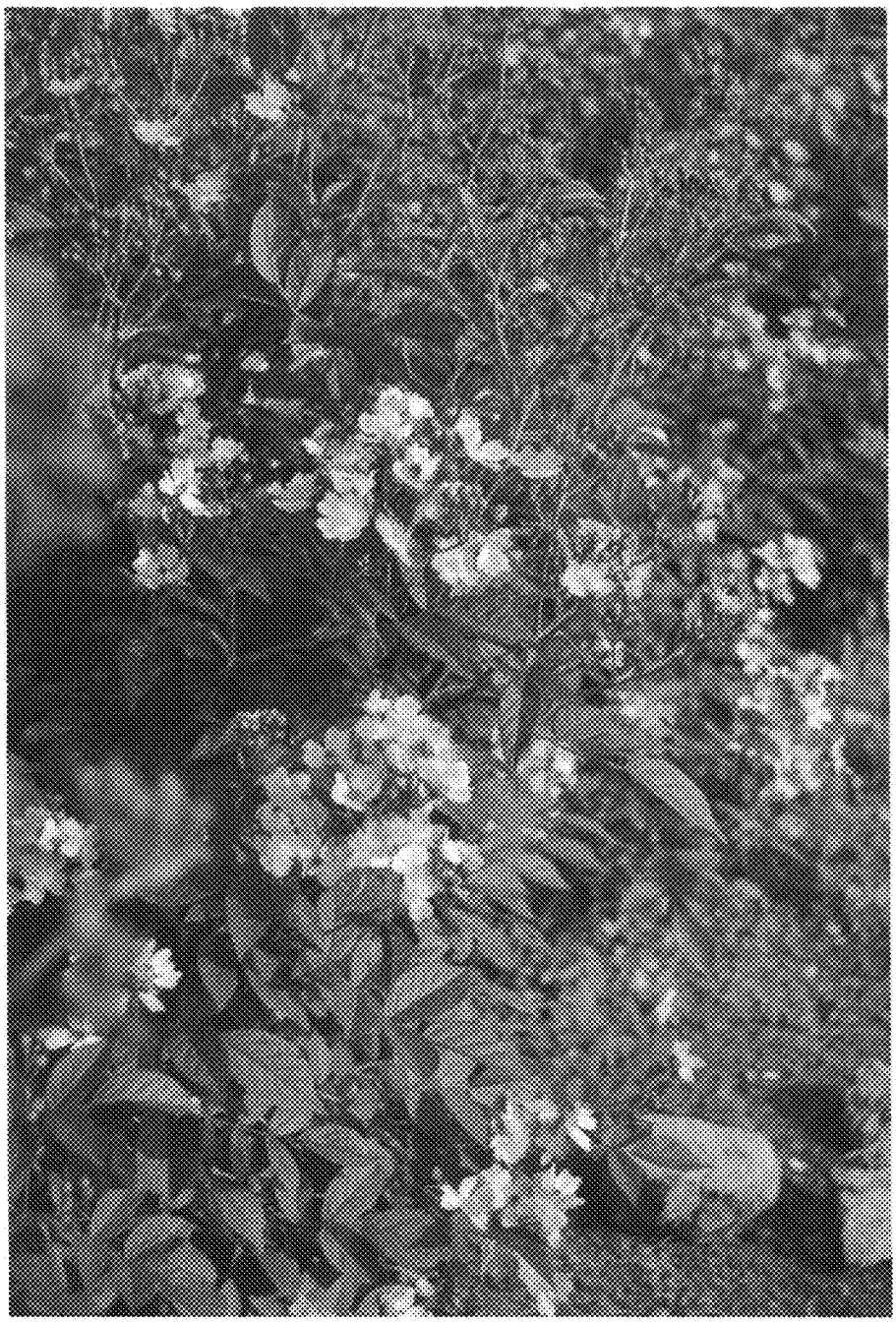

* * * * *